US012582327B2

(12) United States Patent
Sakai et al.

(10) Patent No.: US 12,582,327 B2
(45) Date of Patent: Mar. 24, 2026

(54) PORTABLE NON-CONTACT VITAL SIGNAL DETECTION DEVICE, DRIVER MONITORING DEVICE, VISITOR SCREENING SYSTEM, AND HOME HEALTHCARE SYSTEM

(71) Applicant: SAKURA TECH CORPORATION, Yokohama (JP)

(72) Inventors: Fuminori Sakai, Yokohama (JP); Yasushi Aoki, Yokohama (JP); Mitsuo Makimoto, Yokohama (JP)

(73) Assignee: SAKURA TECH CORPORATION, Yokohama (JP)

( * ) Notice: Subject to any disclaimer, the term of this patent is extended or adjusted under 35 U.S.C. 154(b) by 324 days.

(21) Appl. No.: 18/000,207

(22) PCT Filed: Oct. 8, 2021

(86) PCT No.: PCT/JP2021/037446
§ 371 (c)(1),
(2) Date: Nov. 29, 2022

(87) PCT Pub. No.: WO2022/075467
PCT Pub. Date: Apr. 14, 2022

(65) Prior Publication Data
US 2023/0233090 A1 Jul. 27, 2023

(30) Foreign Application Priority Data
Oct. 9, 2020 (JP) .................................. 2020-171293

(51) Int. Cl.
*A61B 5/0507* (2021.01)
*A61B 5/00* (2006.01)
(Continued)

(52) U.S. Cl.
CPC .......... *A61B 5/0507* (2013.01); *A61B 5/0077* (2013.01); *A61B 5/01* (2013.01);
(Continued)

(58) Field of Classification Search
CPC ....... A61B 5/0507; A61B 5/0077; A61B 5/01; A61B 5/0205; A61B 5/02438; A61B 5/11;
(Continued)

(56) References Cited

U.S. PATENT DOCUMENTS 4,313,119 A * 1/1982 Garay ...................... H01Q 1/38
343/702
5,513,383 A * 4/1996 Tsao ........................ H01Q 1/242
343/702
(Continued)

FOREIGN PATENT DOCUMENTS

JP     2000217792 A     8/2000
JP     2004537335 A     12/2004
(Continued)

OTHER PUBLICATIONS

International Search Report (PCT/ISA/210) with English translation and Written Opinion (PCT/ISA/237) mailed on Dec. 28, 2021, by the Japanese Patent Office as the International Searching Authority for International Application No. PCT/JP2021/037446.
(Continued)

*Primary Examiner* — Ryan W Sherwin
(74) *Attorney, Agent, or Firm* — BUCHANAN, INGERSOLL & ROONEY PC

(57) ABSTRACT
A vital signal detection device includes: an antenna unit provided with a planar antenna of a MIMO radar on a front surface; and a display unit including a display panel on the front surface. The antenna unit is combined with the display unit or the display unit is combined with the antenna unit in
(Continued)

a rotatable manner so that, from a state where the planar antenna and the display panel face in a direction ahead of the front surface, the planar antenna is turned to be directed to a direction of a back surface of the display unit opposite from the display panel. The portable non-contact vital signal detection device detects a vital signal on a side ahead of the front surface and a vital signal on a side in the direction of the back surface opposite from the front surface.

14 Claims, 13 Drawing Sheets

(51) Int. Cl.
| | |
|---|---|
| *A61B 5/01* | (2006.01) |
| *A61B 5/0205* | (2006.01) |
| *A61B 5/024* | (2006.01) |
| *A61B 5/11* | (2006.01) |
| *A61B 5/1171* | (2016.01) |

(52) U.S. Cl.
CPC ........ *A61B 5/0205* (2013.01); *A61B 5/02438* (2013.01); *A61B 5/11* (2013.01); *A61B 5/1176* (2013.01); *A61B 2503/22* (2013.01); *A61B 2505/07* (2013.01)

(58) Field of Classification Search
CPC .............. A61B 5/1176; A61B 2503/22; A61B 2505/07; A61B 5/0022; A61B 2562/0204; A61B 5/02125; A61B 5/0816; A61B 5/721; A61B 5/7445
See application file for complete search history.

(56) References Cited

U.S. PATENT DOCUMENTS

| | | | | |
|---|---|---|---|---|
| 5,867,131 | A | * | 2/1999 | Camp, Jr. ................ H01Q 1/24 |
| | | | | 343/702 |
| 7,388,546 | B2 | * | 6/2008 | Lai ....................... H01Q 1/1257 |
| | | | | 343/702 |
| 2001/0022619 | A1 | * | 9/2001 | Nishiwaki ............ H04N 23/687 |
| | | | | 348/208.99 |
| 2010/0130873 | A1 | * | 5/2010 | Yuen ...................... A61B 5/113 |
| | | | | 600/595 |
| 2016/0156779 | A1 | | 6/2016 | Deshmukh et al. |
| 2018/0122073 | A1 | * | 5/2018 | Redtel .................. A61B 5/0077 |
| 2018/0263502 | A1 | * | 9/2018 | Lin ......................... G01S 7/415 |
| 2018/0348353 | A1 | * | 12/2018 | Lien ...................... G01S 13/003 |
| 2019/0328325 | A1 | | 10/2019 | Parara et al. |
| 2020/0243211 | A1 | * | 7/2020 | Tanaka ..................... G21K 5/10 |
| 2020/0384287 | A1 | * | 12/2020 | Hetz ..................... A61B 5/4848 |
| 2021/0055386 | A1 | * | 2/2021 | Rimini .................. G01S 13/343 |
| 2022/0031172 | A1 | * | 2/2022 | He ........................ H01Q 9/0428 |
| 2022/0218224 | A1 | * | 7/2022 | Shin ..................... A61B 5/0816 |

FOREIGN PATENT DOCUMENTS

| | | | |
|---|---|---|---|
| JP | 2009172176 | A | 8/2009 |
| JP | 2015119770 | A | 7/2015 |
| JP | 2020157000 | A | 10/2020 |

OTHER PUBLICATIONS

Matsumoto, et al., "Research and Development of Vital Sensing Radars", JRC Review, No. 70, 2019, pp. 12-15.

* cited by examiner

Fig.4

Fig.5
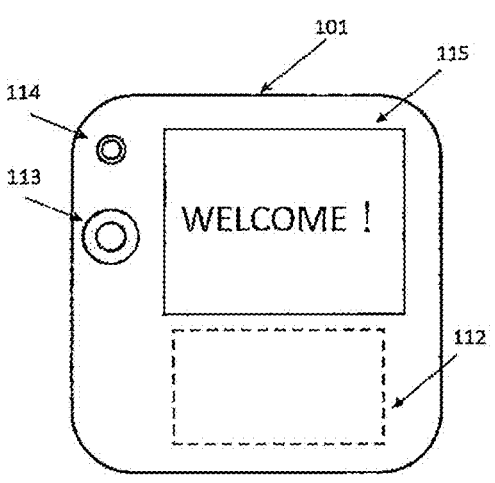
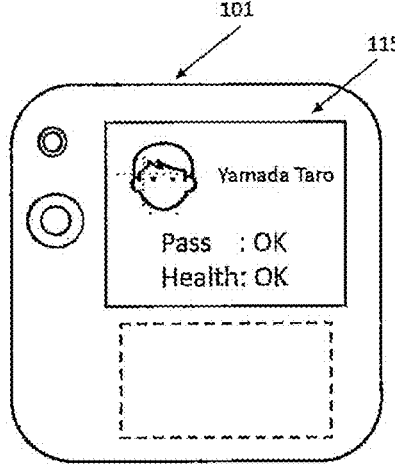
A: DISPLAY DURING AUTHENTICATION          B: DISPLAY OF AUTHENTICATION AND VSM RESULT Fig.6
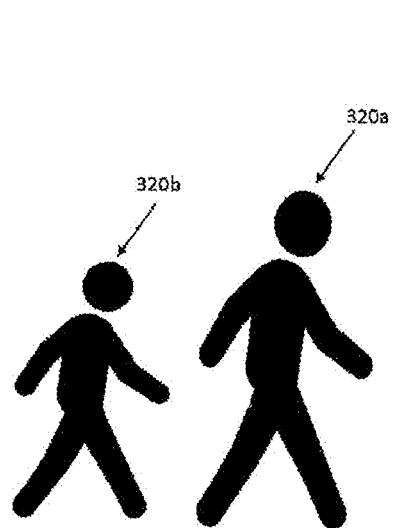
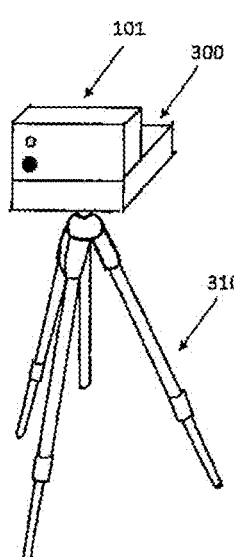

Fig.8

Fig.9 ( a )
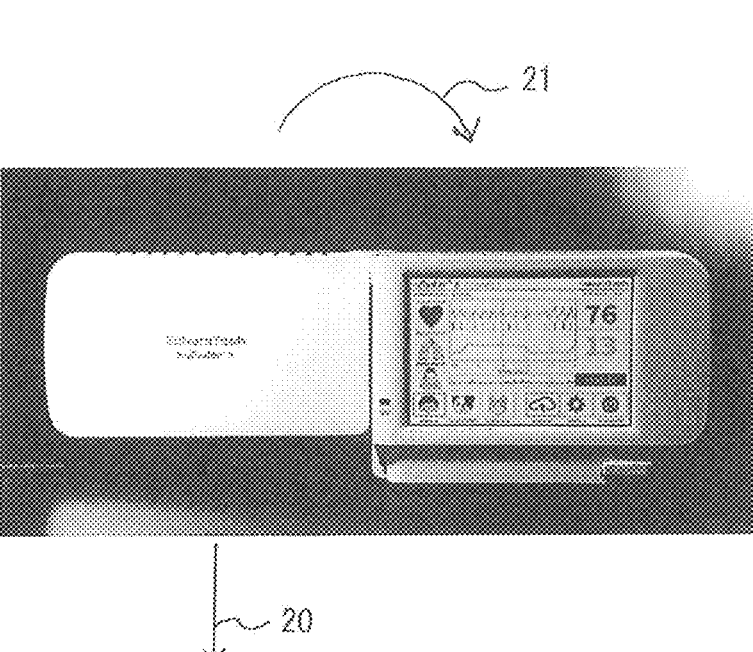
Fig.9 (b)
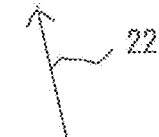
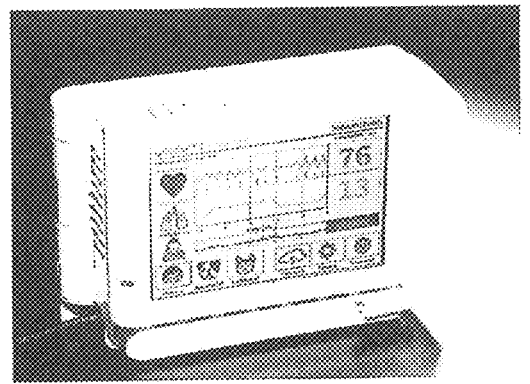

Fig.10 ( a )
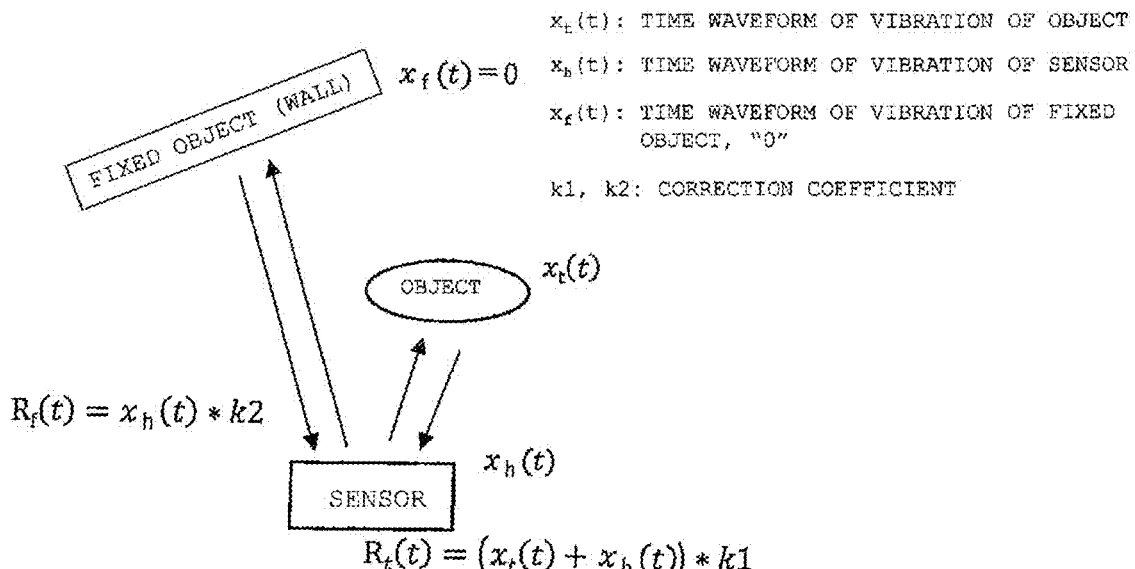
$x_t(t)$: TIME WAVEFORM OF VIBRATION OF OBJECT
$x_h(t)$: TIME WAVEFORM OF VIBRATION OF SENSOR
$x_f(t)$: TIME WAVEFORM OF VIBRATION OF FIXED OBJECT, "0"
k1, k2: CORRECTION COEFFICIENT
RECEPTION SIGNAL OF SENSOR IS EXPRESSED BY FOLLOWING EXPRESSIONS
$$R(t) = R_t(t) + R_f(t)$$
$$R(t) = \left(x_t(t) + x_h(t)\right) * k1 + x_h(t) * k2$$
Fig.10 ( b )
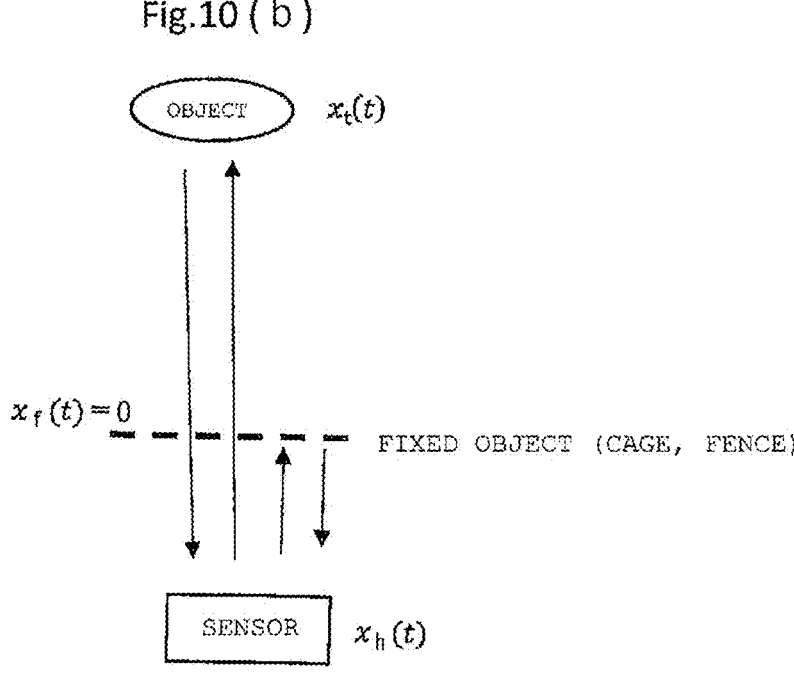

Fig.11 ( a )
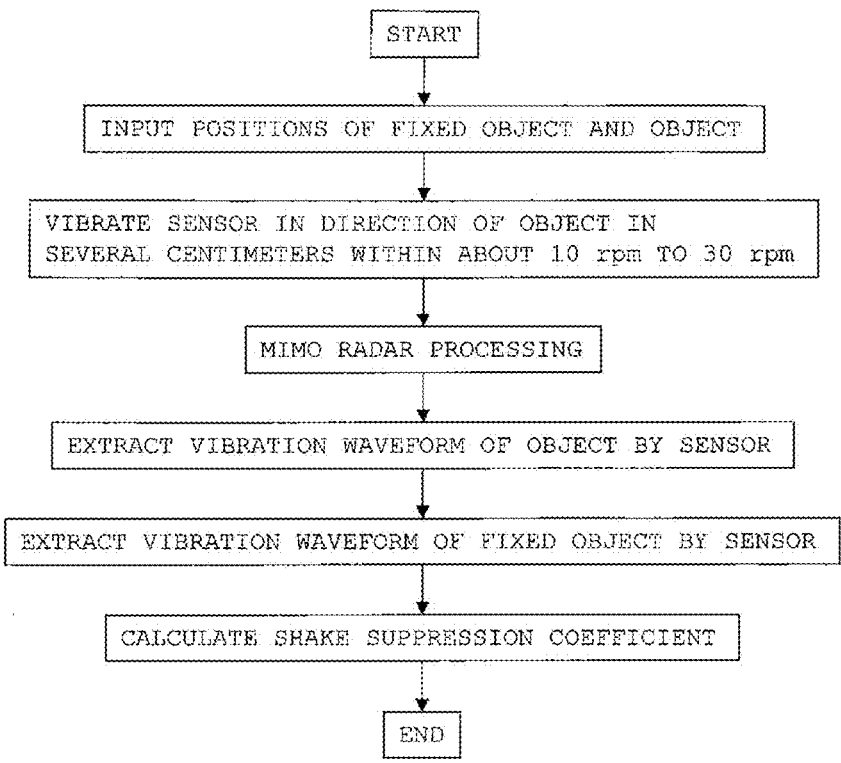
Fig.11 (b)
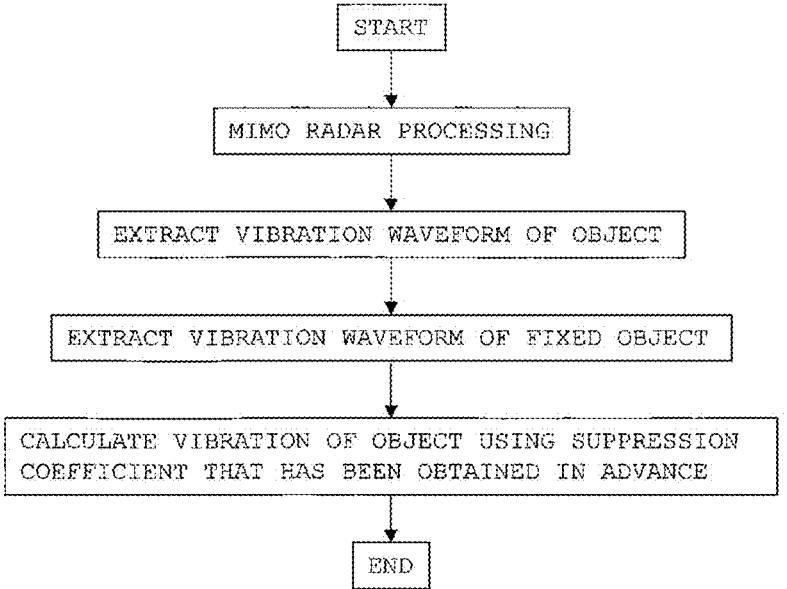

WAVEFORM OF VIBRATION WHEN SENSOR IS
VIBRATED BY SEVERAL CENTIMETERS

PORTABLE NON-CONTACT VITAL SIGNAL DETECTION DEVICE, DRIVER MONITORING DEVICE, VISITOR SCREENING SYSTEM, AND HOME HEALTHCARE SYSTEM

TECHNICAL FIELD

The present invention relates to a compact and portable non-contact vital signal detection device.

BACKGROUND ART

A device that detects vital information such as a body temperature, a heart rate, a respiratory rate, and a blood pressure in a non-contact manner is extremely important not only for work in a hospital, a nursing care facility, or the like, but also for daily health management of an individual, a monitor for a driver's driving condition, or screening of a diseased person in an event venue or transportation facilities where crowded places, close-contact settings, and closed spaces are likely to occur. Therefore, such a device is expected to be widely used.

The body temperature can be easily measured with an infrared thermometer in a non-contact manner. The heart rate and the respiratory rate can be measured in a non-contact manner by a visible light camera or a radar sensor. It is known that a blood pressure can also be estimated in a non-contact manner using a radar sensor. These techniques are also disclosed in the following Patent Literatures.

Patent Literature 1 discloses a method for detecting a body temperature with a radiation thermometer in an ear hole and detecting a heart rate by measuring an electrocardiographic waveform from a potential difference between an ear canal and a palm. The device is compact and portable, but it needs a contact electrode for measurement of the electrocardiographic waveform. Therefore, it is not considered that the heart rate is detected in a non-contact manner. Further, the device does not have a function of detecting a respiratory rate.

Patent Literature 2 discloses an example of an infant incubator that is installed in a hospital and that detects and monitors a vital signal. The incubator is provided with an infrared sensor that detects a body temperature, a visible light camera that detects respiration, heartbeat, and skin blood flow, and a microphone that detects a sound from an infant. All the sensors are individually fixed in the incubator, and contactless measurement is possible, but the incubator is used in a stationary manner.

Patent Literature 3 discloses a method for detecting a diseased body by measuring a body temperature, a respiratory rate, and a heart rate with a stationary non-contact sensor. The temperature is detected with thermography, and the respiratory rate and the heart rate are detected with two different microwave sensors, respectively. The device enables non-contact detection, but is large in size and is used in a stationary manner.

As described above, various methods for measuring a vital signal in a non-contact manner have been disclosed and put into practical use for each vital signal to be detected. However, an integrated device that is portable and that can measure all of a body temperature, a heart rate, a respiratory rate, and a blood pressure has not yet been put into practical use and put into widespread use, although it is expected to be convenient. This is because the integrated device described above has many technical problems.

CITATION LIST

Patent Literature

Patent Literature 1: JP 2000-217792 A
Patent Literature 2: JP 2004-537335 A
Patent Literature 3: JP 2009-172176 A

SUMMARY OF INVENTION

Technical Problem

The present invention provides a non-contact vital signal detection device that is compact, portable, and non-contact, the device enabling detection of vital information from a living body located in front of the non-contact vital signal detection device or from a living body located behind the non-contact vital signal detection device.

It is important in various aspects to acquire vital information such as a body temperature, a respiratory rate, a heart rate, and a blood pressure in a non-contact manner, and when a device used therefor is portable, convenience is greatly improved and new applications can be expected. However, such a device has not yet been put into practical use.

An infrared thermometer can be applied to measure the body temperature in a non-contact manner, and a compact and portable device has been put into practical use. A method of applying a radar sensor is excellent to detect a respiratory rate and a heart rate in a non-contact manner. However, there are many problems regarding being compact and portable, and in order to put a multifunctional portable vital signal detection device into practical use, a reduction in size and portability of a radar sensor and measures against vibration of the device are key problems to be addressed.

Solution to Problem

The present invention provides a non-contact vital signal detection device that is compact and portable and uses a MIMO radar. The non-contact vital signal detection device enables emission of radio waves from the MIMO radar toward the front and toward the rear of the non-contact vital signal detection device, thereby being capable of detecting vital information from a living body located in front of the non-contact vital signal detection device or from a living body located behind the non-contact vital signal detection device.

The non-contact vital signal detection device is compact and portable, and includes an infrared thermometer, a visible light camera, and the like which are provided on the radar sensor.

The present invention enables simple acquisition of a vital signal such as respiration, heartbeat, and body temperature by an independent compact and portable non-contact vital signal detection device.

A compact MIMO radar having a planar antenna is used as the radar sensor.

The present invention employs a configuration including: an antenna unit provided with a planar antenna of a MIMO radar on a front surface; and a display unit including a display panel on the front surface, wherein the antenna unit is combined with the display unit or the display unit is combined with the antenna unit in a rotatable manner so that, from a state where the planar antenna and the display panel face in a direction ahead of the front surface, the planar antenna is turned to be directed to a direction of a back surface of the display unit opposite from the display panel.

The non-contact vital signal detection device detects a vital signal on a side ahead of the front surface and a vital signal on a side in the direction of the back surface.

The present invention provides, as a basic configuration, a portable device capable of detecting not only the respiratory rate and amplitude of a subject whose vital information is to be detected and measured but also the respiration rate and amplitude of a measurer who detects and measures the vital information.

The device is provided with a vibration sensor, and has a function of reducing a detection error due to vibration of the device by acquiring vital information or modifying or correcting acquired information on the basis of vibration information in a front-back direction (a traveling direction of a radar radio wave) of a subject whose vital information is to be detected and measured during measurement.

An infrared thermometer and a visible light camera are mounted on a surface same as the surface of the planar antenna. This configuration achieves a vital signal detection device of a non-contact and portable type that can independently acquire vital information such as body temperature, respiratory rate, and heart rate simultaneously.

The present invention is provided with a correction mechanism that suppresses an influence of shake of the portable non-contact vital signal detection device on a vital signal of the subject detected during detection of the vital signal by a measurer holding the portable non-contact vital signal detection device with his/her hand.

The correction mechanism can suppress, when the measurer performs measurement by holding the portable non-contact vital signal detection device with his/her hand, shake of the portable non-contact vital signal detection device that is superimposed on a signal reflected and returning from the subject using a signal reflected and returning from a fixed object which is near the subject and which is fixed in position.

The present invention described above can be configured as follows.

[1]

A portable non-contact vital signal detection device comprising: an antenna unit provided with a planar antenna of a MIMO radar on a front surface; and a display unit including a display panel on the front surface, wherein the antenna unit is combined with the display unit or the display unit is combined with the antenna unit in a rotatable manner so that, from a state where the planar antenna and the display panel face in a direction ahead of the front surface, the planar antenna is turned to be directed to a direction of a back surface of the display unit opposite from the display panel, and the portable non-contact vital signal detection device detects a vital signal on a side ahead of the front surface and a vital signal on a side in the direction of the back surface opposite from the front surface.

[2]

The portable non-contact vital signal detection device according to [1], further comprising a vibration sensor that detects movement of a living body from which the vital signal is to be detected in a radio wave emission direction of the MIMO radar.

[3]

The portable non-contact vital signal detection device according to [2], wherein the display panel displays a signal level of vibration detected by the vibration sensor.

[4]

The portable non-contact vital signal detection device according to [2] or [3], wherein the vital signal is detected on the basis of a signal regarding vibration detected by the vibration sensor.

[5]

The portable non-contact vital signal detection device according to [2] or [3], wherein the vital signal that has been detected on the basis of a signal regarding vibration detected by the vibration sensor is modified and/or corrected.

[6]

The portable non-contact vital signal detection device according to any one of [1] to [5], wherein the antenna unit is provided with an infrared thermometer that radiates infrared light in a radio wave emission direction of the MIMO radar.

[7]

The portable non-contact vital signal detection device according to any one of [1] to [6], wherein the antenna unit is provided with a visible light camera that captures an image in a radio wave emission direction of the MIMO radar.

[8]

The portable non-contact vital signal detection device according to any one of [1] to [5], wherein the antenna unit is provided with: an infrared thermometer that radiates infrared light in a radio wave emission direction of the MIMO radar; and a visible light camera that captures an image in the radio wave emission direction of the MIMO radar, and respiration, heartbeat, body temperature, and pulse wave velocity are detected as the vital signal.

[9]

The portable non-contact vital signal detection device according to [8], wherein the portable non-contact vital signal detection device acquires a plurality of pieces of pulse wave information as vital information, detects a pulse wave velocity on the basis of the obtained pulse wave information, and estimates a blood pressure from the pulse wave information.

[10]

The portable non-contact vital signal detection device according to any one of [1] to [9], further comprising a correction mechanism that suppresses an influence of shake of the portable non-contact vital signal detection device on the vital signal of a subject detected during detection of the vital signal by a measurer holding the portable non-contact vital signal detection device according to any one of [1] to [9] with his/her hand.

[11]

The portable non-contact vital signal detection device according to [10], wherein the correction mechanism suppresses, when the measurer performs measurement by holding the portable non-contact vital signal detection device with his/her hand, shake of the portable non-contact vital signal detection device that is superimposed on a signal reflected and returning from the subject using a signal reflected and returning from a fixed object which is near the subject and which is fixed in position.

[12]

A driver monitoring device comprising the portable non-contact vital signal detection device according to any one of [1] to [9], the portable non-contact vital signal detection device being provided in a driver's seat of a mobile vehicle, the driver monitoring device monitoring a state of a driver of the mobile vehicle during driving using the portable non-contact vital signal detection device.

[13]

A visitor screening system comprising the portable non-contact vital signal detection device according to [8], the portable non-contact vital signal detection device being installed in a passageway where many people pass, the visitor screening system extracting a diseased person or an unhealthy person from many people passing through the passageway.

[14]

A home healthcare system comprising the portable non-contact vital signal detection device according to any one of [1] to [11], the system enabling a resident to measure and record vital information by himself/herself at home and manage health using the portable non-contact vital signal detection device.

[15]

An access control system comprising the portable non-contact vital signal detection device according to [8], the system performing facial recognition with image information acquired by the visible light camera and detecting and monitoring vital information regarding body temperature, respiration, and heartbeat, using the portable non-contact vital signal detection device.

[16]

An animal health condition monitoring apparatus comprising the portable non-contact vital signal detection device according to any one of [1] to [11], the apparatus detecting vital information of an animal in a zoo or an animal hospital using the portable non-contact vital signal detection device.

Advantageous Effects of Invention

The present invention can provide a non-contact vital signal detection device that is compact and portable and uses a MIMO radar. The non-contact vital signal detection device enables emission of radio waves from the MIMO radar toward the front and toward the rear of the non-contact vital signal detection device, thereby being capable of detecting vital information from a living body located in front of the non-contact vital signal detection device or from a living body located behind the non-contact vital signal detection device.

The present invention can provide a non-contact vital signal detection device that is compact and portable, and includes an infrared thermometer, a visible light camera, and the like which are provided on the radar sensor.

The present invention enables simple acquisition of a vital signal such as respiration, heartbeat, and body temperature by an independent compact and portable non-contact vital signal detection device.

BRIEF DESCRIPTION OF DRAWINGS

FIG. 3 is a diagram illustrating an example in which the portable non-contact vital signal detection device according to the present invention is used in a facility, a hospital, or the like.

FIG. 4 is a diagram illustrating an example in which the portable non-contact vital signal detection device according to the present invention is used for monitoring a driving state of a driver of a vehicle, or the like.

FIG. 5 is a diagram illustrating an example in which the portable non-contact vital signal detection device according to the present invention is used in a control system for controlling an access, or the like, the control system having a facial image recognition function and a health check function.

FIG. 6 is a diagram illustrating an example in which the portable non-contact vital signal detection device according to the present invention is used for screening a diseased person from many people in an event venue or the like.

FIG. 8 is a diagram illustrating an example in which the portable non-contact vital signal detection device according to the present invention is used to detect a vital signal of an animal in, for example, a zoo.

FIG. 9 illustrates reference photographs of a portable non-contact vital signal detection device according to another embodiment of the present invention, wherein FIG. 9($a$) is a reference photograph showing a state in which a planar antenna and a display panel face the direction ahead of a front surface, and FIG. 9($b$) is a reference photograph showing a state in which, from the state illustrated in FIG. 9($a$), the antenna unit is rotated 180 degrees with respect to a display unit so that the planar antenna faces the direction of the back surface of the display unit opposite from the display panel.

FIGS. 10($a$) and 10($b$) are diagrams for describing a correction mechanism that suppresses an influence of shake of the portable non-contact vital signal detection device on a vital signal of a subject detected during detection of the vital signal by a measurer holding the portable non-contact vital signal detection device with his/her hand.

FIG. 11($a$) is a flowchart illustrating processing performed by the correction mechanism until a shake suppression coefficient is calculated, the correction mechanism suppressing an influence of shake of the portable non-contact vital signal detection device on a vital signal of a subject detected during detection of the vital signal by a measurer holding the portable non-contact vital signal detection device with his/her hand, and FIG. 11($b$) is a flowchart illustrating processing of calculating vibration of an object using the calculated shake suppression coefficient.

DESCRIPTION OF EMBODIMENTS

Figure 1:
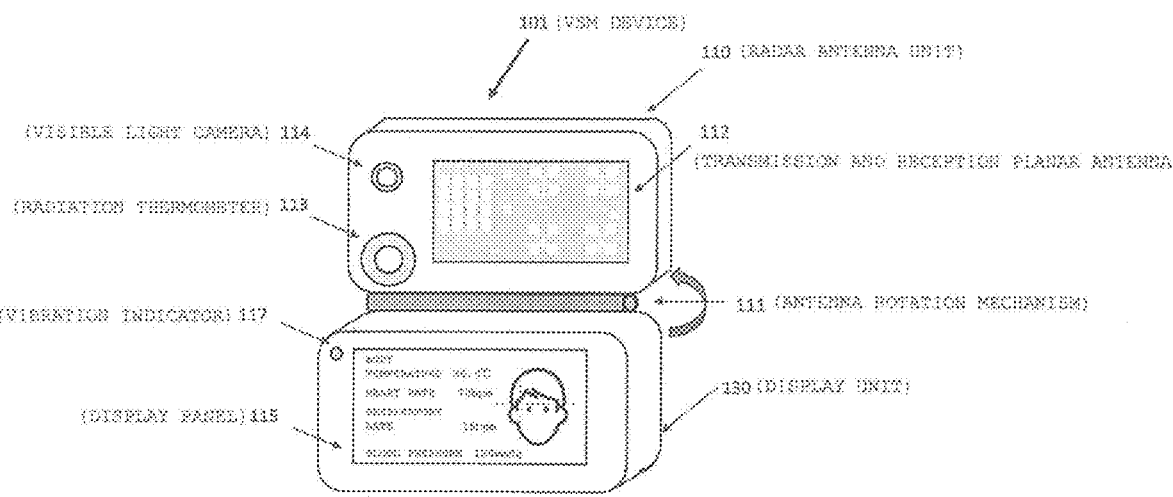
FIG. 1 is a perspective view illustrating an embodiment of a portable non-contact vital signal detection device according to the present invention.

FIG. 1 is a perspective view illustrating an embodiment of a portable non-contact vital signal detection device 101 (which may be referred to as "VSM device" in the specification and drawings) according to the present invention.

The portable non-contact vital signal detection device 101 according to the present embodiment includes an antenna unit 110 and a display unit 130.

The antenna unit 110 includes a planar antenna 112 of a radar on a front surface. The display unit 130 includes a display panel 115 including a liquid crystal display screen or the like on the front surface.

As the radar, a high-resolution radar is adopted, and in the present embodiment, a small-sized multiple input multiple output (MIMO) radar in a microwave or millimeter wave band is adopted. Hereinafter, "multiple input multiple output (MIMO) type radar" may be referred to as "MIMO radar" in the present specification and claims.

The planar antenna 112 is a transmission and reception planar array antenna of a MIMO radar, and is referred to as a transmission and reception planar antenna in FIG. 1.

The planar antenna 112, which is a planar array antenna for transmission and reception of a MIMO radar, transmits and receives radio waves, and detects minute change of an object (that is, a subject) whose vital signal is detected to detect vital information such as respiration and heartbeat.

It has been demonstrated that a MIMO radar can form an antenna with excellent directivity with a small number of antenna elements, and can detect a vital signal with a planar antenna of several centimeters square in a quasi-millimeter wave band of 24 GHz band.

In addition, downsizing and power saving of the device can be achieved due to recent development of semiconductor technology, and thus, feasible performance of a MIMO radar is obtained even when the device is designed to be portable as in the present embodiment.

In normal measurement, a radio wave is emitted to the side ahead of a measurer to detect a vital signal of a subject different from the measurer. On the other hand, when the antenna surface is rotated by 180 degrees, the radio wave is emitted to the rear (toward the measurer), by which the vital signal of the measurer can also be detected.

In the state illustrated in FIG. 1, the planar antenna 112 and the display panel 115 face in the direction ahead of the front surface. The antenna unit 110 is combined with the display unit 130 in a rotatable manner via an antenna rotation mechanism 111. From the illustrated state, the antenna unit 110 can be rotated 180 degrees with respect to the display unit 130 as indicated by an arrow in FIG. 1 such that the planar antenna 112 faces the direction of the back surface of the display unit 130 opposite from the display panel 115.

As a result, the direction of radio wave emitted from the radar can be changed by 180 degrees.

In the state illustrated in FIG. 1, the vital signal on the side ahead of the front surface of the portable non-contact vital signal detection device 101 can be detected. On the other hand, when the antenna unit 110 is rotated 180 degrees with respect to the display unit 130 as indicated by an arrow in FIG. 1, the vital signal in the direction of the back surface opposite from the front surface of the portable non-contact vital signal detection device 101 can also be detected.

In normal measurement, a radio wave is emitted to the side ahead of the measurer to detect a vital signal of a subject different from the measurer. On the other hand, when the antenna surface is rotated 180 degrees, the radio wave is emitted to the rear (toward the measurer), by which the vital signal of the measurer can also be detected.

In the embodiment illustrated in FIG. 1, the antenna unit 110 and the display unit 130 are disposed vertically in the drawing, and the antenna rotation mechanism 111 is interposed between the lower end of the antenna unit 110 and the upper end of the display unit 130. Due to the presence of the antenna rotation mechanism 111, the antenna unit 110 is rotated 180 degrees with respect to the display unit 130.

Thus, the portable non-contact vital signal detection device 101 can be brought into a state in which both the planar antenna 112 and the display panel 115 face forward as illustrated in FIG. 1 and a state (not illustrated) in which the display panel 115 faces forward as illustrated in FIG. 1 and the planar antenna 112 faces the direction of the back surface.

FIG. 9 is a reference photograph showing another embodiment of the portable non-contact vital signal detection device according to the present invention. In FIG. 9(*a*), both the display panel of the display unit on the right side in the drawing and the planar antenna of the antenna unit on the left side in the drawing face forward, and a radio wave of the MIMO radar is emitted from the antenna unit on the left side in the drawing in the direction indicated by an arrow 20. With this mode, a person (measurer) who holds and uses the illustrated portable non-contact vital signal detection device by hand can detect the vital information himself/herself (subject) while viewing the information displayed on the display panel of the display unit on the right side in the drawing.

In the portable non-contact vital signal detection device illustrated in FIG. 9, the antenna rotation mechanism is interposed between the left end of the display unit on the right side in FIG. 9(*a*) and the right end of the antenna unit on the left side in FIG. 9(*a*).

Therefore, when the antenna unit is rotated 180 degrees with respect to the display unit about the portion where the antenna rotation mechanism is provided as indicated by an arrow 21 on the back side of the portable non-contact vital signal detection device in FIG. 9(*a*), the portable non-contact vital signal detection device can be brought into a state in which the planar antenna of the antenna unit faces the direction of the back surface of the display unit opposite from the display panel as illustrated in FIG. 9(*b*).

With this state, a radio wave of the MIMO radar is emitted from the planar antenna of the antenna unit in the direction indicated by an arrow 22 in FIG. 9(*b*). The measurer holding the portable non-contact vital signal detection device can detect the vital information of the subject located in the direction of the arrow 22 while viewing the information displayed on the display panel of the display unit as illustrated in FIG. 9(*b*).

As illustrated in FIG. 9(*b*), the measurer who holds and operates the portable non-contact vital signal detection device by hand (person who performs measurement) can detect vital information of the subject by radio waves emitted from the MIMO radar to the subject from the planar antenna of the antenna unit in a direction indicated by the arrow 22 in FIG. 9(*b*) while viewing information displayed on the display panel of the display unit.

As described with reference to FIG. 9, the portable non-contact vital signal detection device 101 according to the present embodiment is so compact that a person who performs measurement can perform measurement by holding it in hand. Therefore, the transmission wave may be emitted not only forward but also backward as indicated by arrows 20 and 22 in FIGS. 9(*a*) and 9(*b*).

There is no problem when the measurer measures himself/herself by turning the antenna so that the antenna faces the measurer as illustrated in FIG. 9(*a*). However, when an object (subject) located in the direction of the arrow 22 is measured as illustrated in FIG. 9(*b*), a transmission wave is also emitted backward (in the direction opposite to the direction of the arrow 22), and the device may receive the vibration of the measurer himself/herself.

In view of this, in a case where the device is used as illustrated in FIG. 9(*b*), a shielding plate (not illustrated) can be interposed between the antenna unit and the display unit.

In this configuration, the shielding plate is interposed and easily fixed between the display unit (the front side in FIG. 9(*b*)) and the antenna unit (the rear side in FIG. 9(*b*)) in the state illustrated in FIG. 9(*b*), and the shielding plate can be easily removed when the device is returned from the state illustrated in FIG. 9(*b*) to the state illustrated in FIG. 9(*a*).

When a thin plate-shaped shielding plate (not illustrated) is present between the display unit (the front side in FIG. 9(*b*)) and the antenna unit (the rear side in FIG. 9(*b*)) in the state illustrated in FIG. 9(*b*), the radiation of the radio wave to the rear (in the direction opposite to the direction of the arrow 22) can be reduced.

This configuration can prevent the radiation of transmission wave to the rear and prevent the device from receiving the vibration of the measurer himself/herself during measurement of the object (subject) located in the direction of the arrow 22 as illustrated in FIG. 9(*b*).

Figure 2:
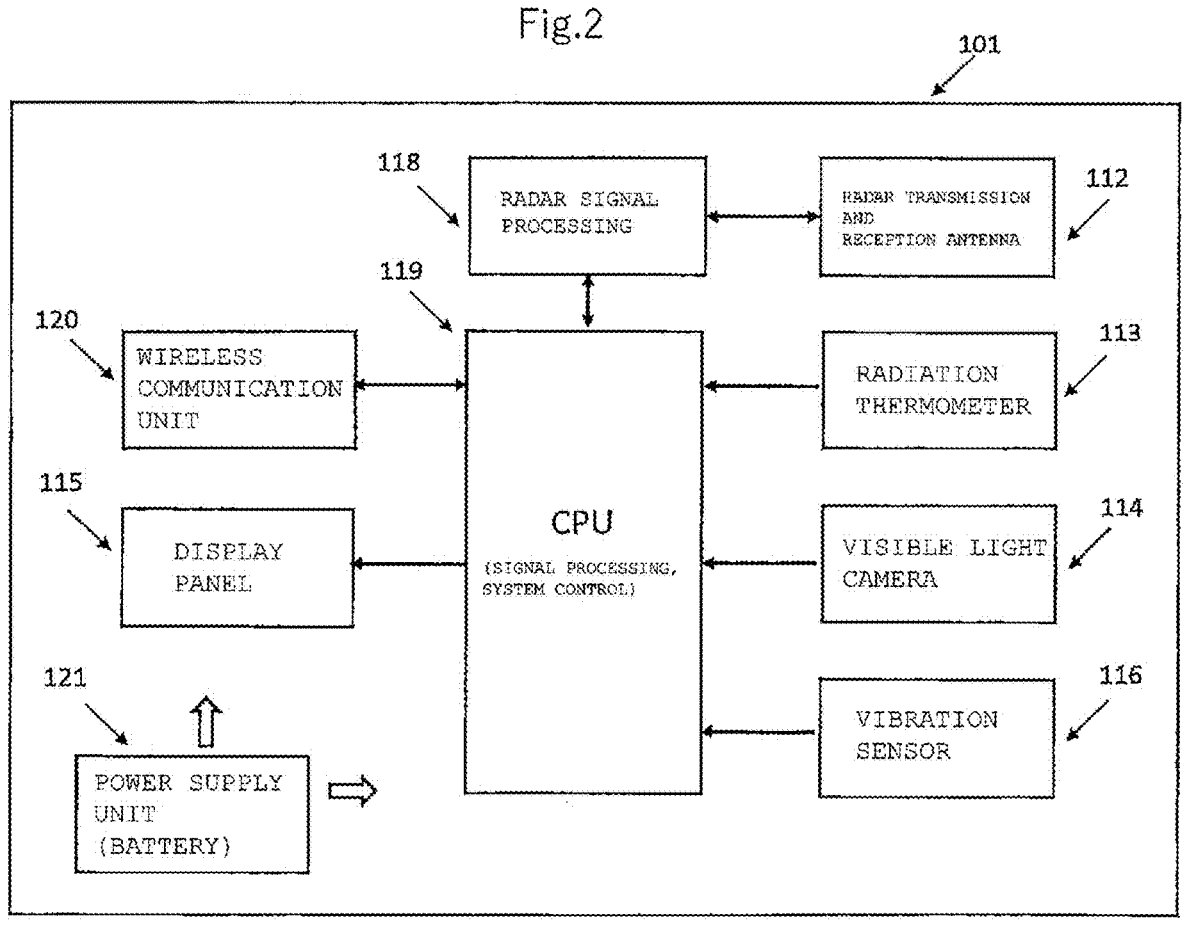
FIG. 2 is a block diagram illustrating an example of a circuit configuration of the portable non-contact vital signal detection device illustrated in FIG. 1.

FIG. 2 is a block diagram illustrating an example of a circuit configuration of the portable non-contact vital signal detection device 101 illustrated in FIG. 1.

Similar to smartphones or the like, the portable non-contact vital signal detection device 101 can have a computer function of executing various functions described later under a predetermined computer program.

In the embodiment illustrated in FIG. 2, the portable non-contact vital signal detection device 101 includes a radar signal processing unit 118, a central processing unit (CPU) (signal processing, system control) 119, a wireless communication unit 120 necessary for connection with the outside, and a power supply unit 121. Depending on the usage mode, the portable non-contact vital signal detection device 101 can be provided with a storage device, a backup power supply, an installation device when used in a portable semi-stationary manner, or the like as an accessory device.

The radar signal processing unit 118 can analyze amplitude information and frequency information from the radar signal acquired by the planar antenna 112, which is a transmission and reception planar array antenna of the MIMO radar, and acquire information regarding the respiratory rate and the heart rate of the subject.

In addition, derived information such as pulse wave velocity and blood pressure can be estimated from the acquired radar signal by predetermined processing performed by the radar signal processing unit 118 and the CPU (signal processing, system control) 119.

The portable non-contact vital signal detection device 101 according to the embodiment illustrated in FIG. 1 can be provided with a vibration sensor that detects movement of a living body (subject) from which the vital signal is detected in a radar radio wave emission direction.

When the respiratory rate or the heart rate of the subject is actually measured using the MIMO radar, it is desirable to fix the radar and detect minute displacement (about 1 mm) of the radio wave in the traveling direction (that is, in the front-back direction of the subject) of the radio wave toward the subject. In addition, the radar is required to be stably held for several seconds, because the breathing cycle is around 3 seconds.

When the portable non-contact vital signal detection device 101 that can be operated by the measurer with his/her hand is used as in the present embodiment, the radar itself also shakes. Therefore, an anti-shake measure is extremely important.

A commercially available visible light camera also has an anti-shake (vibration) measure. However, in this case, the shake in the vertical and horizontal directions of the camera with respect to a subject is a problem, whereas the shake in the front-back direction which is the direction from the camera to the subject hardly matters. In addition, the visible light camera has a much shorter correction time for the shake as compared with the radar.

Therefore, the anti-shake (vibration) measure conventionally adopted in the visible light camera is not a technique applicable to the anti-shake measure of the present invention.

In view of this, in the present embodiment, a vibration sensor 116 is provided in the device (in particular, the antenna unit 110) to detect a vibration level in the radar radio wave emission direction (front-back direction of the subject), thereby detecting the movement of the living body (subject) from which the vital signal is detected in the radar radio wave emission direction.

As the vibration sensor 116, a three-dimensional acceleration meter or the like can be employed.

The signal level of the vibration detected by the vibration sensor 116 can be displayed on the display panel 115. Alternatively, the signal level of the vibration detected by the vibration sensor 116 can be displayed by a vibration indicator 117. The signal level can also be displayed in both the display panel 115 and the vibration indicator 117.

The vital signal can be detected on the basis of the signal regarding the vibration detected by the vibration sensor 116. In addition, the vital signal detected on the basis of the signal regarding vibration detected by the vibration sensor 116 can be modified and/or corrected.

The portable non-contact vital signal detection device 101 can be provided with a function of performing measurement only when the measurement is possible as a result of the detection of the vibration level in the radar radio wave emission direction (front-back direction of the subject) by the vibration sensor 116. Alternatively, the portable non-contact vital signal detection device 101 corrects original detection information obtained by the radar using vibration information obtained by the vibration sensor 116 to extract accurate information regarding respiration and heartbeat.

The portable non-contact vital signal detection device 101 can be provided with a mechanism for suppressing occurrence of an error caused by the shake being superimposed on a signal of an object in a case where the measurer performs measurement by holding the portable non-contact vital signal detection device 101 with his/her hand.

This mechanism can be mounted on the portable non-contact vital signal detection device 101 separately from the configuration in which the original detection information obtained by the radar is corrected using the vibration information obtained by the vibration sensor 116 described above to extract accurate information regarding respiration and heartbeat. Alternatively, this mechanism can be mounted on the portable non-contact vital signal detection device 101 in addition to the configuration in which the original detection information obtained by the radar is corrected using the vibration information obtained by the vibration sensor 116 described above to extract accurate information regarding respiration and heartbeat.

This mechanism is a correction mechanism that suppresses an influence of the shake of the portable non-contact vital signal detection device 101 on the vital signal of the subject detected during detection of the vital signal by the measurer holding the portable non-contact vital signal detection device 101 with his/her hand.

In a case where the measurer performs measurement by holding the portable non-contact vital signal detection device 101 with his/her hand, shake of the portable non-contact vital signal detection device 101 may be superimposed on the signal of the object. In this case, a measurement error occurs.

This phenomenon can be prevented by the mechanism for suppressing occurrence of an error caused by the shake being superimposed on a signal of an object in a case where the measurer performs measurement by holding the portable non-contact vital signal detection device 101 with his/her hand.

This mechanism is, for example, a correction mechanism that, when the measurer performs measurement by holding the portable non-contact vital signal detection device 101 with his/her hand, suppresses the shake of the portable non-contact vital signal detection device 101 that is superimposed on a signal reflected and returning from the subject using a signal reflected and returning from a fixed object.

This correction mechanism will be described with reference to FIGS. 10 and 11. Two points that are a fixed object and a subject which is indicated as an "object" in FIGS. 10(*a*) and 10(*b*) are set as measurement points measured by the portable non-contact vital signal detection device indicated as a "sensor" in FIGS. 10(*a*) and 10(*b*) according to the present embodiment.

In FIG. 10(*a*), a wall which is near the object (subject) and which is fixed in position is used as the fixed object. In FIG. 10(*b*), a cage or fence which is near the object (subject) and which is fixed in position is used as the fixed object.

First, the positions of the fixed object and the object are input to the portable non-contact vital signal detection device (FIG. 11(*a*)). For example, the positions of the fixed object and the object can be input to the portable non-contact vital signal detection device in such a manner that, for example, the radar signals acquired from the fixed object and the object with respect to the radio wave of the MIMO radar emitted from the radar transmission/reception antenna 112 are stored in the storage unit of the portable non-contact vital signal detection device and read by processing of the radar signal processing unit 118, the CPU 119, and the like.

Next, the sensor (portable non-contact vital signal detection device) is vibrated in the direction of the object (subject) in several centimeters (FIG. 11(*a*)). For example, the sensor (portable non-contact vital signal detection device) is vibrated in the direction of the object (subject) in several centimeters within about 10 rpm to 30 rpm.

As a result, a signal reflected and returning from the object (subject) and a signal reflected and returning from the fixed object are processed by the sensor (portable non-contact vital signal detection device). This process is referred to as "MIMO radar processing" in FIG. 11(*a*). That is, the vibration waveform of the object and the vibration waveform of the fixed object are extracted from the radar signal acquired by the sensor (portable non-contact vital signal detection device) with respect to the radio wave of the MIMO radar emitted from the radar transmission/reception antenna 112 by the processing of the radar signal processing unit 118, the CPU 119, and the like, and a shake suppression coefficient is calculated (FIG. 11(*a*)).

The steps so far are preparation steps. When the measurement is performed, an influence of the shake of the portable non-contact vital signal detection device 101 on the vital signal of the subject detected during detection of the vital signal by the measurer holding the portable non-contact vital signal detection device 101 with his/her hand can be suppressed according to an operation flow illustrated in FIG.

11(*b*) using the shake suppression coefficient calculated in the steps in FIG. 11(*a*). Thus, more accurate vibration of the subject can be measured.

As illustrated in FIG. 10(*a*), a reception signal $R_t(t)$ received from the object by the sensor (portable non-contact vital signal detection device) is expressed by Expression (1).

$$R_t(t)=x_t(t)\times k_1+x_h(t)\times k_1 \tag{1}$$

In Expression (1), $x_t(t)$ is a time waveform of vibration of the object, $x_h(t)$ is a time waveform of vibration of the sensor, and $k_1$ is a correction coefficient.

A reception signal $R_f(t)$ received from the fixed object by the sensor (portable non-contact vital signal detection device) is expressed by $$R_f(t)=x_f(t)\times k_2+x_h(t)\times k_2$$

where $x_f(t)$ is a time waveform of vibration of the fixed object, $x_h(t)$ is a time waveform of vibration of the sensor, and $k_2$ is a correction coefficient.

Here, $x_f(t)=$time waveform of the vibration of the fixed object$=0$, and thus, Expression (2) is established.

$$R_f(t)=x_f(t)\times k_2+x_h(t)\times k_2=x_h(t)\times k_2 \tag{2}$$

Therefore, a reception signal $R(t)$ of the sensor (portable non-contact vital signal detection device) is expressed as follows.

$$R(t) = R_t(t) + R_f(t) \tag{3}$$
$$= (x_t(t)\times k_1 + x_h(t))\times k_1 + x_h(t)\times k_2$$

In this Expression, $x_h(t)\times k_1$ is a measured value of the vibration waveform of the object (IF waveform), and $x_h(t)\times k_2$ is a measured value of the vibration waveform of the fixed object (IF waveform).

Figure 12:
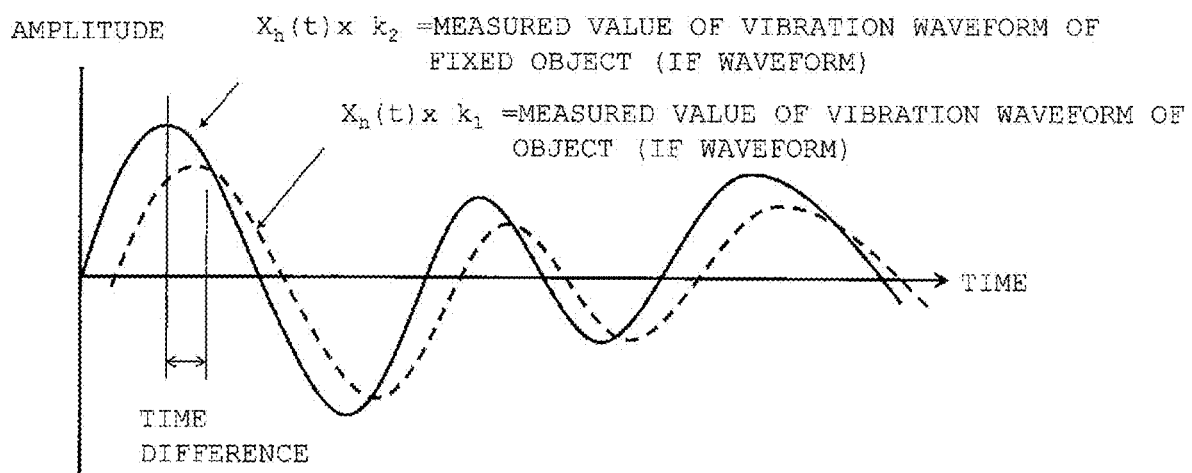
FIG. 12 is a diagram for describing a vibration waveform from a fixed object and a vibration waveform from an object with the correction mechanism that suppresses an influence of shake of the portable non-contact vital signal detection device on a vital signal of a subject detected during detection of the vital signal by a measurer holding the portable non-contact vital signal detection device with his/her hand.

As described in FIG. 12, the sensor is vibrated in the direction of the object (subject) in centimeters. For example, when the sensor is vibrated in the direction of the object (subject) in several centimeters within about 10 rpm to 30 rpm, the vibration waveform of the object is sufficiently smaller than the vibration waveform of the sensor and can be ignored.

Therefore, when $k_3$ that satisfies $x_h(t)\times k_1+x_h(t)\times k_2\times k_3=0$ is obtained, following Expression (4) is obtained.

$$k_3=-\{x_h(t)\times k_1\}\div\{x_h(t)\times k_2\} \tag{4}$$

$k_3$ is a conversion coefficient, that is, shake suppression coefficient, for obtaining the shake of the hand included in the measured value of the vibration waveform of the object from the measured value of the vibration waveform of the fixed object.

When the conversion coefficient $k_3$ is used, Expression (4) (reception signal $R(t)$ of the sensor) described above can be expressed as follows.

$$R(t)=x_t(t)\times k_1+\{x_h(t)\times k_1+x_h(t)\times k_2\times k_3\} \tag{5}$$

As described above, $k_3$ that satisfies $x_h(t)\times k_1+x_h(t)\times k_2\times k_3=0$ is obtained (Expression (4)). Therefore, when $k_3=-\{x_h(t)\times k_1\}\div\{x_h(t)\times k_2\}$ obtained by above Expression (4) is used, it is possible to suppress the shake of the hand included in the time waveform of the vibration of the object.

That is, the reception signal R(t) of the sensor (portable non-contact vital signal detection device) is expressed by following Expression (5).

$$R(t) = x_t(t) \times k_1 + \{x_h(t) \times k_1 + x_h(t) \times k_2 \times k_3\}$$

$$= x_t(t) \times k_1 + 0$$

$$= x_t(t) \times k_1$$

As described above, an influence of the shake of the portable non-contact vital signal detection device 101 on the vital signal of the subject detected during detection of the vital signal by the measurer holding the portable non-contact vital signal detection device 101 with his/her hand can be suppressed by calculating the above-mentioned $k_3$ (shake suppression coefficient).

The correction mechanism that suppresses an influence of the shake of the portable non-contact vital signal detection device 101 on the vital signal of the subject detected during detection of the vital signal by the measurer holding the portable non-contact vital signal detection device 101 with his/her hand can be implemented by the above processing performed by the radar signal processing unit 118, the CPU 119, or the like provided to the portable non-contact vital signal detection device 101.

As illustrated in FIG. 1, an infrared thermometer 113 that radiates infrared light in the radar radio wave emission direction can be provided in the antenna unit 110. Due to the infrared thermometer 113, the body temperature of the subject can be measured in a non-contact manner.

Furthermore, as illustrated in FIG. 1, a visible light camera 114 that captures an image in the radar radio wave emission direction can be provided in the antenna unit 110.

The facial image of the person to be measured (subject) can be displayed on the display panel 115 by the visible light camera 114, the measurement distance and the measurement site can be determined by the image information during the measurement of the vital signal to improve the accuracy of the measurement signal, and a function of specifying the person to be measured by the facial image recognition technology can be provided.

Furthermore, a change in blood flow in the face can also be detected, whereby pulse wave information can be further acquired, and this function can also be incorporated in the device.

Thus, it is possible to detect vital signals of respiration, heartbeat, body temperature, and pulse wave velocity by the portable non-contact vital signal detection device 101 independently.

In addition, it is also possible to detect the pulse wave velocity from the above-described information regarding the respiratory rate, the heart rate, and the like of the subject obtained from the radar signal and a plurality of pieces of pulse wave information obtained by the visible light camera 114, and estimate the blood pressure from the pulse wave information.

The portable non-contact vital signal detection device 101 according to the present embodiment uses the MIMO radar, and thus, it is possible to individually and simultaneously acquire vibration continuously from a plurality of different parts of the human body of the subject using a microwave radar sensor.

Therefore, it is possible to improve measurement accuracy by performing processing of individually and simultaneously acquiring vibrations continuously from a plurality of different parts of the human body of the subject, calculating a heartbeat interval (RPI) from vibration waveforms of the plurality of parts of the subject, and excluding a singular value.

A processing control unit including the CPU 119 or the like performs processing of calculating a heartbeat interval (RPI) from vibration waveforms of a plurality of parts of the subject, calculating an average value and a standard deviation, excluding a value having the heartbeat interval (RPI) of $1\sigma$ or more, and calculating an average value of remaining portions to improve measurement accuracy, for example.

Figure 13:
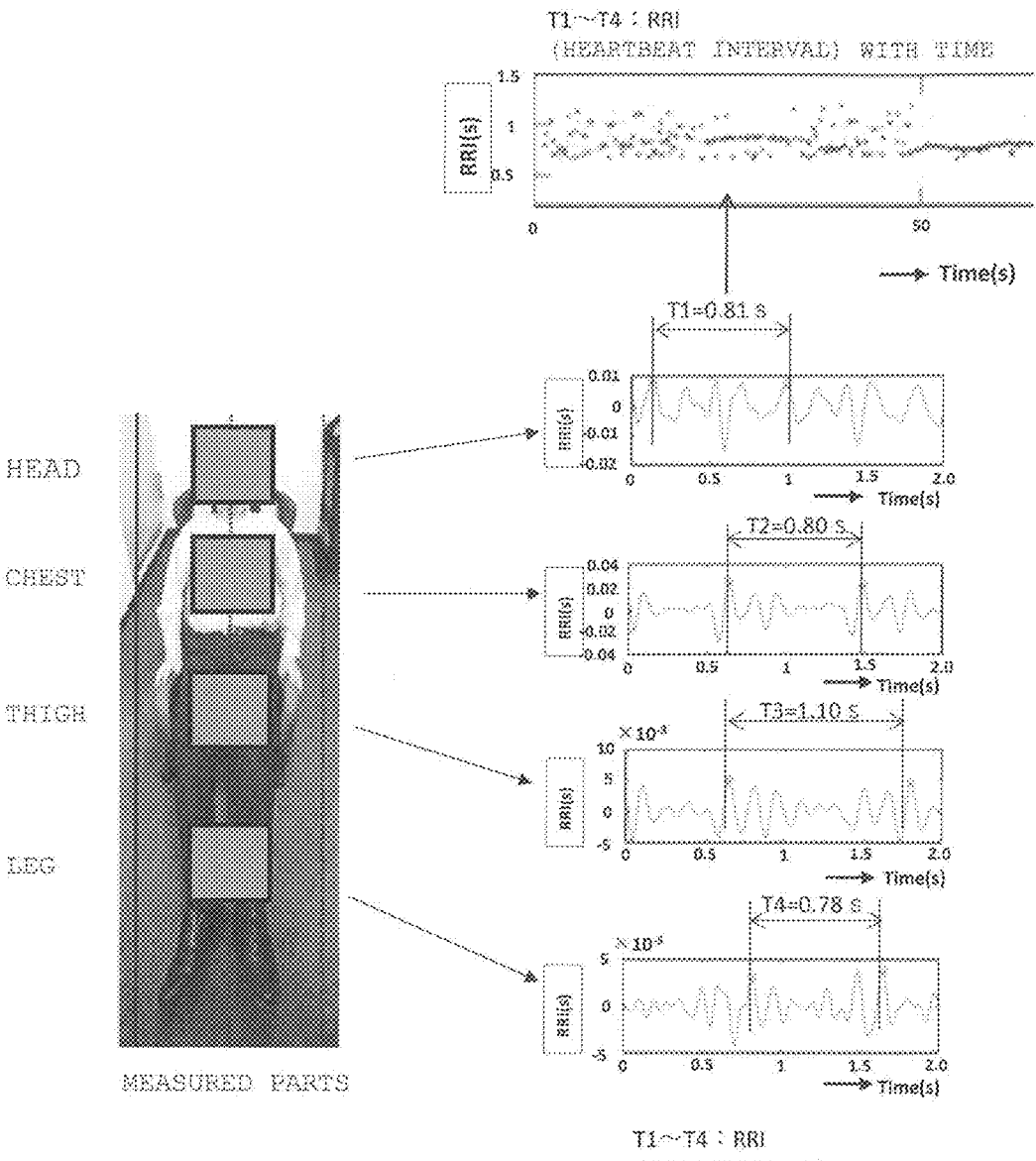
FIG. 13 is a conceptual diagram illustrating a method for improving measurement accuracy of a heartbeat interval (RRI) by vibration information acquired from a plurality of parts of a subject.

In FIG. 13, vibrations are acquired individually, simultaneously, and continuously from a plurality of parts (head, chest, thigh, leg) of the subject. The average value of T1 (head), T2 (chest), T3 (thigh), and T4 (leg) in FIG. 13 is 0.8725 s and the standard deviation is 0.1317 s. In this case, when the value having $1\sigma$ or more is excluded and the average value is recalculated to obtain a heartbeat interval (RPI), the heartbeat interval (RPI) is 0.7966 s.

These calculation processing results and the like can be displayed on the display unit 130.

By a predetermined computer program that causes a computer to execute the various functions described above, predetermined processing is executed by the radar signal processing unit 118 and the CPU (signal processing, system control) 119, and the various types of processing described above are executed on the basis of the radar signal acquired by the planar antenna 112, the vibration information acquired by the vibration sensor 116, the temperature information acquired by the infrared thermometer, and the image information acquired by the visible light camera 114. Thus, the portable non-contact vital signal detection device 101 can independently detect and measure the respiration, heartbeat, and body temperature and estimate the pulse wave velocity and blood pressure.

Note that the display panel 115 can have a function of displaying measurement conditions and data of the detected vital signal in addition to the image of the subject.

The feature in which the portable non-contact vital signal detection device 101 can independently acquire basic vital information such as the respiratory rate, the heart rate, and the body temperature as described above greatly improves the convenience of measurement, and further, greatly contributes to safety and labor saving of measurement work. Thus, the application range can be greatly expanded. In addition, the present invention can be applied not only for business use but also for healthcare in daily life at home.

The utilization modes of the present invention will be described below with reference to some examples, but the present invention is not limited to the above-described embodiment and the examples described below, and various modifications are possible within the technical scope understood from the description of the claims.

Examples of Use in Facilities, Hospitals, and the Like

Figure 3:
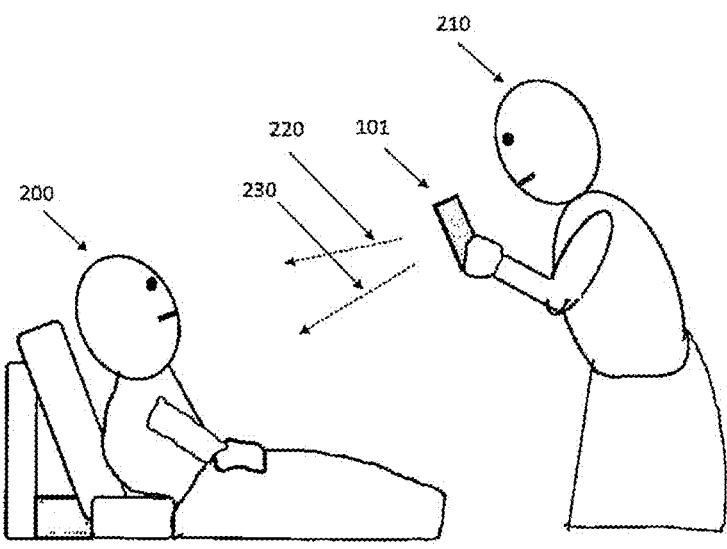

FIG. 3 illustrates an example in which a nurse, a care worker, or the like always carries the portable non-contact vital signal detection device 101 according to the above-described embodiment in a hospital, a nursing care facility, or the like, and uses the portable non-contact vital signal detection device when checking the health condition of a patient or the like. FIG. 3 illustrates an example of a method for detecting the respiratory rate and the heart rate of a patient or the like at the chest.

FIG. 3 illustrates the portable non-contact vital signal detection device 101 according to the above-described embodiment, a subject 200, a measurer 210 such as a nurse or a care worker, a measurement direction 220 of a facial image and a body temperature, and a radar radio wave emission direction 230 toward the chest.

In this manner, the respiratory rate and the heart rate can be detected at the chest of the subject 200.

With the portable non-contact vital signal detection device 101 according to the above embodiment, it is possible to detect the body temperature, the respiratory rate, and the heart rate and estimate the blood pressure in a non-contact manner, and this enables safety and simple nursing and care services.

According to the portable non-contact vital signal detection device 101 according to the above embodiment, a heartbeat signal can be measured from the displacement of the chest by the radar, and the pulse wave information can be detected from a blood flow change of the face by the visible light camera 114.

It is known that the pulse wave velocity can be detected by comparing signals of two parts of the human body as described above and examining a correlation. In view of this, a necessary computer program is mounted on the signal processing unit including a computer of the portable non-contact vital signal detection device 101 according to the above embodiment, by which the brain wave velocity can be detected.

In addition, it is also known that the pulse wave velocity can be detected using heartbeat signals of two parts, the chest and the head, by utilizing the multi-beam function of the MIMO radar, and this method can also be applied.

It is physiologically known that there is a correlation between the pulse wave velocity and the maximum blood pressure, and an approximate value of the maximum blood pressure can be estimated by detecting the pulse wave velocity by such a method.

The feature in which such basic vital information can be acquired by a single device is extremely useful in care services.

Monitoring of Driving State of Driver of Vehicle or the Like

Figure 4:
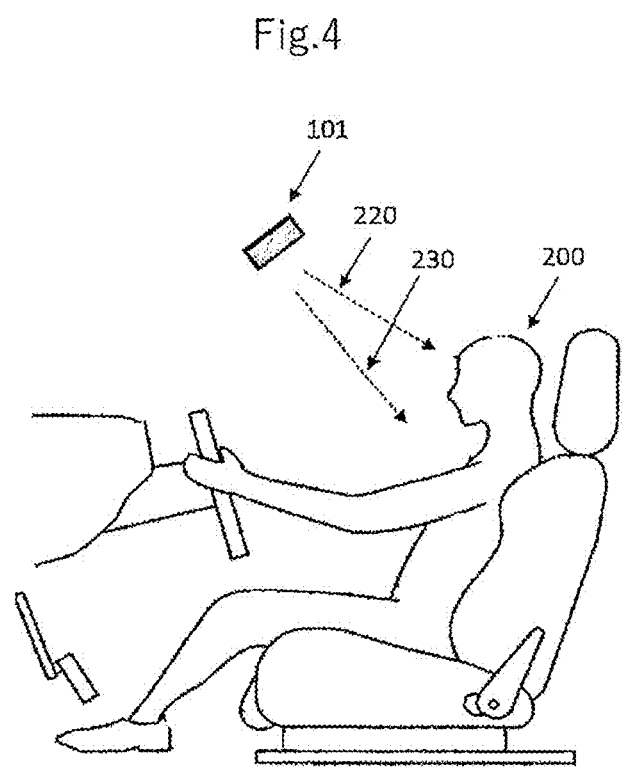

FIG. 4 illustrates an application example in which the portable non-contact vital signal detection device 101 according to the above embodiment is applied to a driving state monitor or a dozing detector for a bus driver, a taxi driver, a driver of public transportation, or the like utilizing the features of the portable non-contact vital signal detection device 101.

This is an example in which the present invention is applied as a driver monitoring device that monitors the state (for example, health condition) of a driver of a mobile vehicle during driving by the portable non-contact vital signal detection device 101 according to the above embodiment mounted in the driver's seat of the mobile vehicle.

FIG. 4 illustrates the portable non-contact vital signal detection device 101 according to the above-described embodiment, a subject (driver) 200, a measurement direction 220 of a facial image and a body temperature, and a radar radio wave emission direction 230. FIG. 4 illustrates a method for detecting the respiratory rate and the heart rate at the chest.

An example in which vital information is acquired by an individual sensor such as a camera or a radar device is known as a driver's driving condition monitor, but such example has many problems regarding an installation place, wiring, and the like when being mounted in a narrow interior of the vehicle.

FIG. 4 illustrates an example in which the portable non-contact vital signal detection device 101 according to the above-described embodiment is mounted above the driver's seat.

By applying such a small device, a degree of freedom of selecting an installation location is increased. Further, the body temperature, respiration, heartbeat, face information, and the like are acquired simultaneously, whereby the driving condition of the driver can be recognized more accurately and quickly, and dozing or the like can be detected extremely effectively. Thus, the portable non-contact vital signal detection device 101 has higher utility value in terms of safety.

This example shows the case in which the portable non-contact vital signal detection device 101 according to the above-described embodiment is mounted above the driver's seat. Note that, although this example shows that the present invention is applied to public transportation, it is obvious that the present invention is applicable to monitor the driving of an individual driver of a private car.

Application to Access Control System Having Facial Image Recognition Function and Health Check Function FIG. 5 illustrates an example of application to an access control system having a health check function as well as a facial image recognition function.

The access control system uses the portable non-contact vital signal detection device 101 according to the above embodiment to perform facial recognition using image information acquired by the visible light camera 114 and to detect and monitor vital information regarding the body temperature, the respiration, and the heartbeat.

FIG. 5 illustrates the portable non-contact vital signal detection device 101 according to the above embodiment, the transmission and reception planar antenna 112, the radiation thermometer 113, the visible light camera 114, and the display panel 115. In FIG. 5, A on the left side illustrates a display example during authentication/measurement, and B on the right side illustrates a display example of the authentication result and the vital signal measurement result.

In the application described above, being portable is not so important, but being non-contact and compact is important. Thus, the application described above can utilize the feature of the present invention of being mounted at any place and being easily changed in installation state.

This application is supposed to use a system that compares a facial image with an external database via a network during facial image recognition. Due to such system, safe and secure access control is enabled in hospitals or nursing care facilities that need continuous management of vital information and health condition of an individual person on a daily basis, places of business handling food, or the like.

Example of Application to Screening for Diseased Persons from Many People at Event Venue or the Like FIG. 6 illustrates an application example to a system for screening a diseased person in a place where many people are gathered such as an event venue or a stadium.

This example shows a visitor screening system that includes the portable non-contact vital signal detection device 101 according to the above embodiment which is installed in a passageway where many people pass, the visitor screening system extracting a diseased person or an unhealthy person from many people passing through the passageway.

FIG. 6 illustrates the portable non-contact vital signal detection device 101 according to the above embodiment, an installation device (installation base) 300 for the portable non-contact vital signal detection device, a portable tripod stand 310, and visitors (subjects) 320*a* and 320*b*.

In order to accurately detect a person suspected of having infection as seen in the case of COVID-19, it is desirable to perform comprehensive check by detecting not only the body temperature as has been conventionally done but also vital signals such as respiration and heartbeat.

This can be achieved by applying the portable non-contact vital signal detection device 101 which is compact and portable and of a non-contact type according to the present invention.

FIG. 6 shows an example in which, in a case where many people are screened in a large facility, a backup power supply, a communication device, and the like are also provided to a portable installation device such as a tripod stand, and an installation place and the number of devices to be installed are appropriately selected to enable continuous measurement for a long time.

Application Examples at Home, Room, etc.

Figure 7:
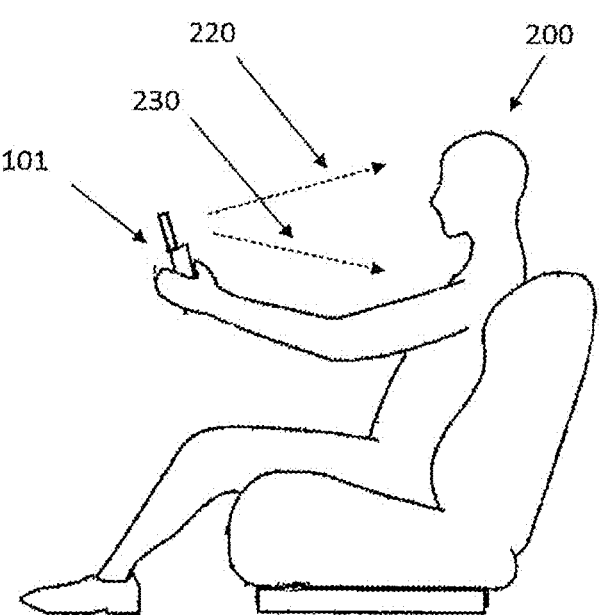
FIG. 7 is a diagram illustrating an example in which the portable non-contact vital signal detection device according to the present invention is used for a health management monitor at home or in a room.

FIG. 7 illustrates an example of application to a daily health care monitor at home.

This example shows a home healthcare system in which a resident measures and records vital information by himself/herself at home and manages his/her health using the portable non-contact vital signal detection device 101 according to the above embodiment.

FIG. 7 illustrates the portable non-contact vital signal detection device 101 according to the above-described embodiment, a person to be measured (subject, in this case, measurer himself/herself) 200, a facial image capturing direction 220, and a radar radio wave beam direction 230 toward the chest.

At home, health management is often performed by measuring a body temperature, a heartbeat, a blood pressure, and the like on a daily basis, but these items are often measured using a plurality of sensors.

By using the portable non-contact vital signal detection device 101 which is of a portable and non-contact type according to the present invention, it is possible to perform measurement by oneself regardless of the location and collectively obtain vital information. Thus, convenience is improved and labor-saving is achieved, so that the present invention can contribute to continuous health management.

This example shows a situation in which the subject measures by himself/herself by rotating the antenna surface 180 degrees, while sitting on a sofa in a living room. However, the subject can perform measurement at any place such as a toilet or a washroom.

In addition, in a case where a user does training with slow movement such as yoga or qigong in a room, he/she does the training while constantly monitoring the vital signal by the portable VSM according to the present invention mounted on a tripod stand or the like, whereby he/she can do the training effectively.

The example in which the user measures his/her vital signal by oneself has been described above. However, it is obvious that the present invention can be used as a home healthcare device on a daily basis. For example, the user measures the vital signal of another person, for example, a parent checks the health condition of his/her child, by bringing the antenna into a normal state.

Example of Application for Detecting Vital Signal of Animal in Zoo or the Like The following is an embodiment in which the portable non-contact vital signal detection device 101 according to the above embodiment is used as an animal health condition monitoring apparatus that detects vital information of an animal in a zoo or an animal hospital.

Figure 8:
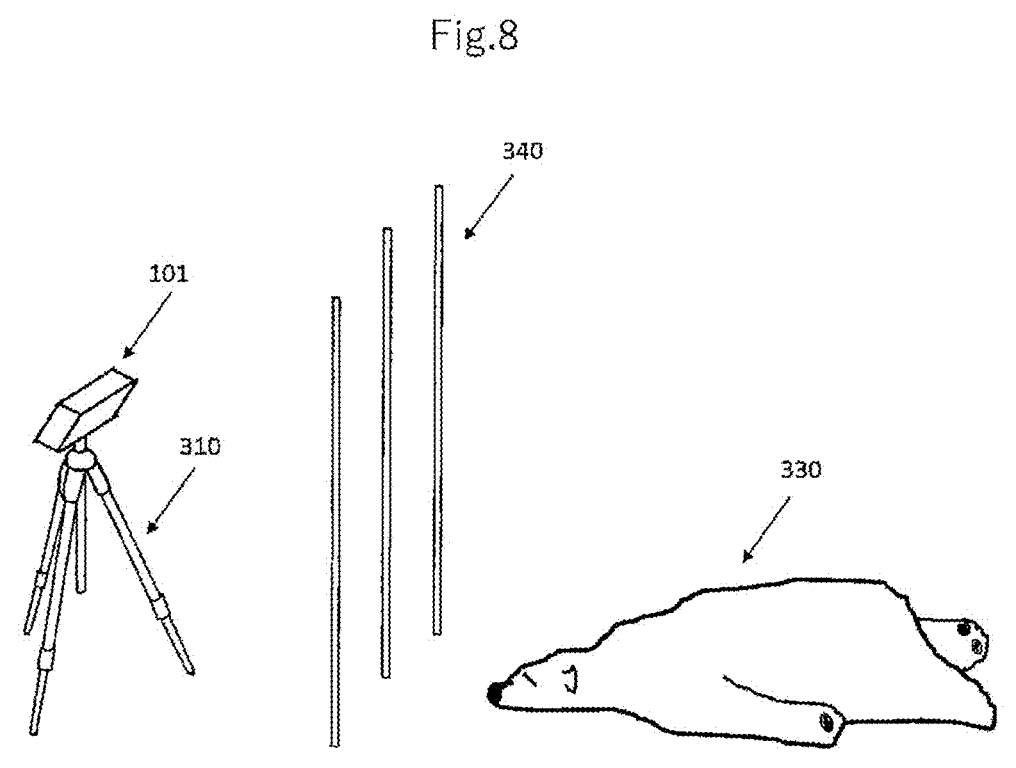

FIG. 8 illustrates an example of application for detecting the vital signal of an animal in a zoo or the like.

FIG. 8 illustrates the portable non-contact vital signal detection device 101 according to the above embodiment, a portable tripod stand 310 on which the portable non-contact vital signal detection device 101 is mounted, an animal to be measured 330, and a cage 340.

In zoos or animal hospitals, a measured vital signal of an animal is important data for checking the health condition and for investigating the ecology of the animal. Meanwhile, dangerous animals that inflict harm are likely to be treated, and thus, it is essential that a measurer such as a breeding staff performs measurement in a non-contact manner from a safe place.

Utilizing the feature of the present invention of being non-contact and portable enables measurement of an ecological signal of an animal safely and easily. FIG. 8 illustrates an example in which the portable non-contact vital signal detection device 101 is mounted on a tripod stand and installed near an animal to be measured (may be installed outside a cage as illustrated in FIG. 8) for measurement.

As with humans, information regarding the body temperature (infrared thermometer) and blood flow change (visible light camera) can be obtained from the face of an animal, and information regarding respiration and heartbeat can be obtained by the radar. There are many animals to be measured having hairy body surface. However, the hairy body surface hardly affects radio waves, and thus, the measurement with the radar can be performed without any problem, and basic vital information such as a respiratory rate, a heart rate, or a pulse wave velocity can be obtained.

INDUSTRIAL APPLICABILITY

An integrated vital signal detector device of a compact and portable type has not yet been put into practical use. The present invention achieves the compact and portable type as described above. Thus, the present invention contributes to improvement of convenience of workers in hospitals and nursing care facilities, increase in safety, and reduction of a work load, and further the use thereof is greatly expanded in various works and daily health management which need information regarding a vital signal.

The present invention achieves an integrated vital signal detector device of a non-contact and portable type that can detect body temperature, respiratory rate, and heart rate and estimate a blood pressure. Thus, the present invention contributes to improvement of convenience of workers in hospitals and nursing care facilities, increase in safety, and reduction of a work load for inspection, and further the use thereof is greatly expanded in an application which needs information regarding a vital signal.

For example, by utilizing the feature of being portable and enabling integral and simultaneous measurement in a non-contact manner, the present invention can monitor the condition (for example, health condition) of a driver during driving, perform health check when a worker enters or leaves an office or a factory, perform screening to extract a diseased person or an unhealthy person in an event venue or a transportation facility where crowded places, close-contact settings, and closed spaces are likely to occur, and detect the vital signal of a measurer himself/herself. Thus, the present invention can be widely used for daily health care at home and the like.

The invention claimed is:

1. A portable non-contact vital signal detection device comprising:

an antenna unit provided with a planar antenna of a MIMO radar;

a display unit including a display panel; and a correction mechanism that is configured to suppress an influence of shake of the portable non-contact vital signal detection device on the vital signal of a subject detected during detection of the vital signal by a measurer holding the portable non-contact vital signal detection device with his/her hand, wherein the antenna unit is combined with the display unit or the display unit is combined with the antenna unit in a rotatable manner so that, from a state where the planar antenna and the display panel face in a same forward direction, the planar antenna is configured to be turned to be directed to a rearward direction opposite the forward direction, the portable non-contact vital signal detection device is configured to detect a vital signal in the forward direction or a vital signal in the rearward direction, and the correction mechanism is configured to suppress, when the measurer performs measurement by holding the portable non-contact vital signal detection device with his/her hand, shake of the portable non-contact vital signal detection device that is superimposed on a signal reflected and returning from the subject using a signal reflected and returning from a fixed object which is near the subject and which is fixed in position.

2. The portable non-contact vital signal detection device according to claim 1, further comprising a vibration sensor that detects movement of a living body from which the vital signal is to be detected in a radio wave emission direction of the MIMO radar.

3. The portable non-contact vital signal detection device according to claim 2, wherein the display panel displays a signal level of vibration detected by the vibration sensor.

4. The portable non-contact vital signal detection device according to claim 2, wherein the vital signal is detected on the basis of a signal regarding vibration detected by the vibration sensor.

5. The portable non-contact vital signal detection device according to claim 2, wherein the vital signal that has been detected on the basis of a signal regarding vibration detected by the vibration sensor is modified and/or corrected.

6. The portable non-contact vital signal detection device according to claim 1, wherein the antenna unit is provided with an infrared thermometer that radiates infrared light in a radio wave emission direction of the MIMO radar.

7. The portable non-contact vital signal detection device according to claim 1, wherein the antenna unit is provided with a visible light camera that captures an image in a radio wave emission direction of the MIMO radar.

8. The portable non-contact vital signal detection device according to claim 1, wherein the antenna unit is provided with: an infrared thermometer that radiates infrared light in a radio wave emission direction of the MIMO radar; and a visible light camera that captures an image in the radio wave emission direction of the MIMO radar, and respiration, heartbeat, body temperature, and pulse wave velocity are detected as the vital signal.

9. The portable non-contact vital signal detection device according to claim 8, wherein the portable non-contact vital signal detection device acquires a plurality of pieces of pulse wave information as vital information, detects a pulse wave velocity on the basis of the obtained pulse wave information, and estimates a blood pressure from the pulse wave information.

10. A visitor screening system comprising the portable non-contact vital signal detection device according to claim 8, the portable non-contact vital signal detection device being installed in a passageway where many people pass, the visitor screening system extracting a diseased person or an unhealthy person from many people passing through the passageway.

11. An access control system comprising the portable non-contact vital signal detection device according to claim 8, the system performing facial recognition with image information acquired by the visible light camera and detecting and monitoring vital information regarding body temperature, respiration, and heartbeat, using the portable non-contact vital signal detection device.

12. A driver monitoring device comprising the portable non-contact vital signal detection device according to claim 1, the portable non-contact vital signal detection device being provided in a driver's seat of a mobile vehicle, the driver monitoring device monitoring a state of a driver of the mobile vehicle during driving using the portable non-contact vital signal detection device.

13. A home healthcare system comprising the portable non-contact vital signal detection device according to claim 1, the system enabling a resident to measure and record vital information by himself/herself at home and manage his/her health using the portable non-contact vital signal detection device.

14. An animal health condition monitoring apparatus comprising the portable non-contact vital signal detection device according to claim 1, the apparatus detecting vital information of an animal in a zoo or an animal hospital using the portable non-contact vital signal detection device.

* * * * *